United States Patent
Bristow (10) Patent No.: US 9,809,555 B2
(45) Date of Patent: Nov. 7, 2017

(54) FORM OF MEFENPYR-DIETHYL, A PROCESS FOR ITS PREPARATION AND USE OF THE SAME

(71) Applicant: ROTAM AGROCHEM INTERNATIONAL COMPANY LIMITED, Chai Wan, Hong Kong (CN)

(72) Inventor: James Timothy Bristow, Hong Kong (CN)

(73) Assignee: ROTAM AGROCHEM INTERNATIONAL COMPANY LIMITED, Chai Wan (HK)

(*) Notice: Subject to any disclaimer, the term of this patent is extended or adjusted under 35 U.S.C. 154(b) by 20 days.

(21) Appl. No.: 14/956,991

(22) Filed: Dec. 2, 2015

(65) Prior Publication Data

US 2017/0158641 A1 Jun. 8, 2017

(51) Int. Cl.
*C07D 231/06* (2006.01)
*A01N 43/56* (2006.01)
*A01N 47/36* (2006.01)
*A01N 25/32* (2006.01)

(52) U.S. Cl.
CPC .......... *C07D 231/06* (2013.01); *A01N 43/56* (2013.01); *A01N 47/36* (2013.01)

(58) Field of Classification Search
CPC .................................................. C07D 231/06
See application file for complete search history.

(56) References Cited

U.S. PATENT DOCUMENTS

| | | | | |
|---|---|---|---|---|
| 5,571,772 A * | 11/1996 | Willms | .................. | A01N 47/36 504/106 |
| 5,703,008 A | 12/1997 | Rosch et al. | | |
| 5,908,938 A * | 6/1999 | Schlegel | .............. | C07D 231/06 548/379.4 |
| 6,420,381 B1 * | 7/2002 | Muraoka | ............... | C07D 471/04 514/300 |
| 2015/0031877 A1 * | 1/2015 | Hiratsuka | ............... | A01N 43/84 544/105 |
| 2015/0223461 A1 | 8/2015 | Frenzel et al. | | |

FOREIGN PATENT DOCUMENTS

| | | |
|---|---|---|
| CN | 1052115 A | 6/1991 |
| CN | 1269791 A | 10/2000 |
| CN | 102816118 A | 12/2012 |
| CN | 104797577 A | 7/2015 |

OTHER PUBLICATIONS

McClurg, R.B., "X-Ray Powder Diffraction (XRPD) to Describe Crystal Forms," Publication of SSCI an Aptuit Company, Jul. 9, 2008, pp. 1-23.*
Roberts, R.M. et al. Modern Experimental Organic Chemistry. Holt, Rinehart and Winston, New York, 1979, pp. 49-58.*
Cossack WG 15 MSDS, Bayer CropScience, Jun. 30, 2015.*
International Search Report and Written Opinion for PCT/CN2016/098337 dated Nov. 30, 2016.

* cited by examiner

*Primary Examiner* — John Pak
(74) *Attorney, Agent, or Firm* — Dickinson Wright PLLC (57) ABSTRACT

A crystalline form of mefenpyr-diethyl of formula (I), the crystal preparation process, the analyses of the crystal through various analytical methods and using the crystal to prepare stable agrochemical formulation. The invention also describes the use of various solvents towards the crystalline form preparation conditions.

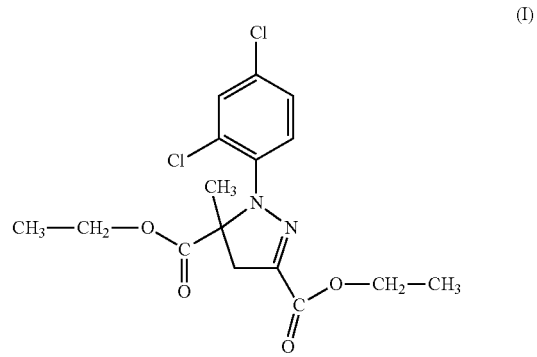

(I)

15 Claims, 4 Drawing Sheets

FORM OF MEFENPYR-DIETHYL, A PROCESS FOR ITS PREPARATION AND USE OF THE SAME

BACKGROUND

Field

The present disclosure relates to a crystalline form of diethyl (RS)-1-(2,4-dichlorophenyl)-5-methyl-2-pyrazoline-3,5-dicarboxylate (mefenpyr-diethyl), to its preparation processes and to its use in agrochemical preparations.

Description of Related Art

Mefenpyr-diethyl, i.e., diethyl (RS)-1-(2,4-dichlorophenyl)-5-methyl-2-pyrazoline-3,5-dicarboxylate is a potent safener for sulfonylurea herbicides. Mefenpyr-diethyl has molecular formula of $C_{16}H_{18}Cl_2N_2O_4$. Its chemical structure is:

(I)

It is typically used to reduce the phototoxicity of sulfonylurea herbicides when applied on crops, such as maize, wheat and cereals.

The commercially available mefenpyr-diethyl, which is usually manufactured by the process described in U.S. Pat. No. 5,703,008, which is incorporated herein by reference for all purposes, is present in an amorphous state.

SUMMARY

It has been found that mefenpyr-diethyl in amorphous state is highly unstable. It will generally undergo significant hydrolysis when dissolved or dispersed in water. Furthermore, hydrolysis can occur during storage, particularly where the compound is exposed to moisture. As a result, the stability of mefenpyr-diethyl is of great concern with respect to providing the commercially available formulations. Therefore, there is a need to provide a novel form mefenpyr-diethyl with increased stability in formulations.

Accordingly, in an embodiment, the invention provides a novel crystalline form of mefenpyr-diethyl, termed "crystalline modification I", and a process for its preparation, as well as its use in agrochemical compositions. The novel crystalline modification I has been found to have increased stability relative to the amorphous form. Accordingly, in an embodiment, the invention also provides compositions for controlling undesirable plant growth, such as weeds, comprising the crystalline modification I of mefenpyr-diethyl with sulfonylurea herbicides, as a mixture with auxiliaries and carriers. The use of the crystalline modification I of mefenpyr-diethyl with sulfonylurea herbicides in the control of undesired plant growth and a method for the same are also provided by embodiments of the invention.

BRIEF DESCRIPTION OF DRAWINGS

Various aspects of the invention can be more clearly understood by reference to the drawings, which are described below, and are intended to be illustrative, not limiting, of the invention.

DETAILED DESCRIPTION OF SPECIFIC EMBODIMENTS

The embodiments and aspects of the invention disclosed herein can be more clearly understood by the following detailed description of specific embodiments and examples, which are intended to illustrate, but not limit, the scope of the appended claims.

It has been found that the crystalline modification I of mefenpyr-diethyl has a significant increase in its stability when mixing with sulfonylurea herbicides in formulations that are otherwise similar to current commercially available formulations, which contain the amorphous form of mefenpyr-diethyl. In addition, it has been found that the crystalline modification I of mefenpyr-diethyl is easier to comminute or grain compared to amorphous mefenpyr-diethyl prepared in accordance with the disclosure of U.S. Pat. No. 5,703,008, which is incorporated herein by reference for all purposes. This allows the preparation of commercial formulations such as suspension concentrates (SC), oil-based suspension concentrates (OD), water-dispersible granules (WG) and water-soluble granules (SG). Hence, it is possible to prepare any formulations of mefenpyr-diethyl in crystalline modification I when mixing with sulfonylurea herbicides, as will be disclosed in more details hereinafter.

By virtue of its high stability, the crystalline modification I of mefenpyr-diethyl when mixing with sulfonylurea herbicides is highly suitable for preparing compositions for controlling undesirable weeds.

According to an embodiment of the invention, a crystalline modification I of mefenpyr-diethyl is provided, exhibiting at least 3 of the following reflexes as 2θ values, in any combination thereof, in an X-ray powder diffractogram recorded using Cu-Kα radiation at 25° C.:

| | |
|---|---|
| 2θ=7.76±0.2 | (1) |
| 2θ=10.76±0.2 | (2) |
| 2θ=14.00±0.2 | (3) |
| 2θ=14.85±0.2 | (4) |
| 2θ=16.67±0.2 | (5) |
| 2θ=19.49±0.2 | (6) |
| 2θ=23.10±0.2 | (7) |
| 2θ=23.75±0.2 | (8) |

$2\theta=24.48\pm0.2$ (9)

$2\theta=26.02\pm0.2$ (10)

$2\theta=26.27\pm0.2$ (11)

$2\theta=28.49\pm0.2$ (12)

The X-ray powder diffractogram was taken using a diffractometer in reflection geometry in the range from 3°-60° with increments of 0.03° using Cu-Kα radiation at 25° C.

Figure 2:
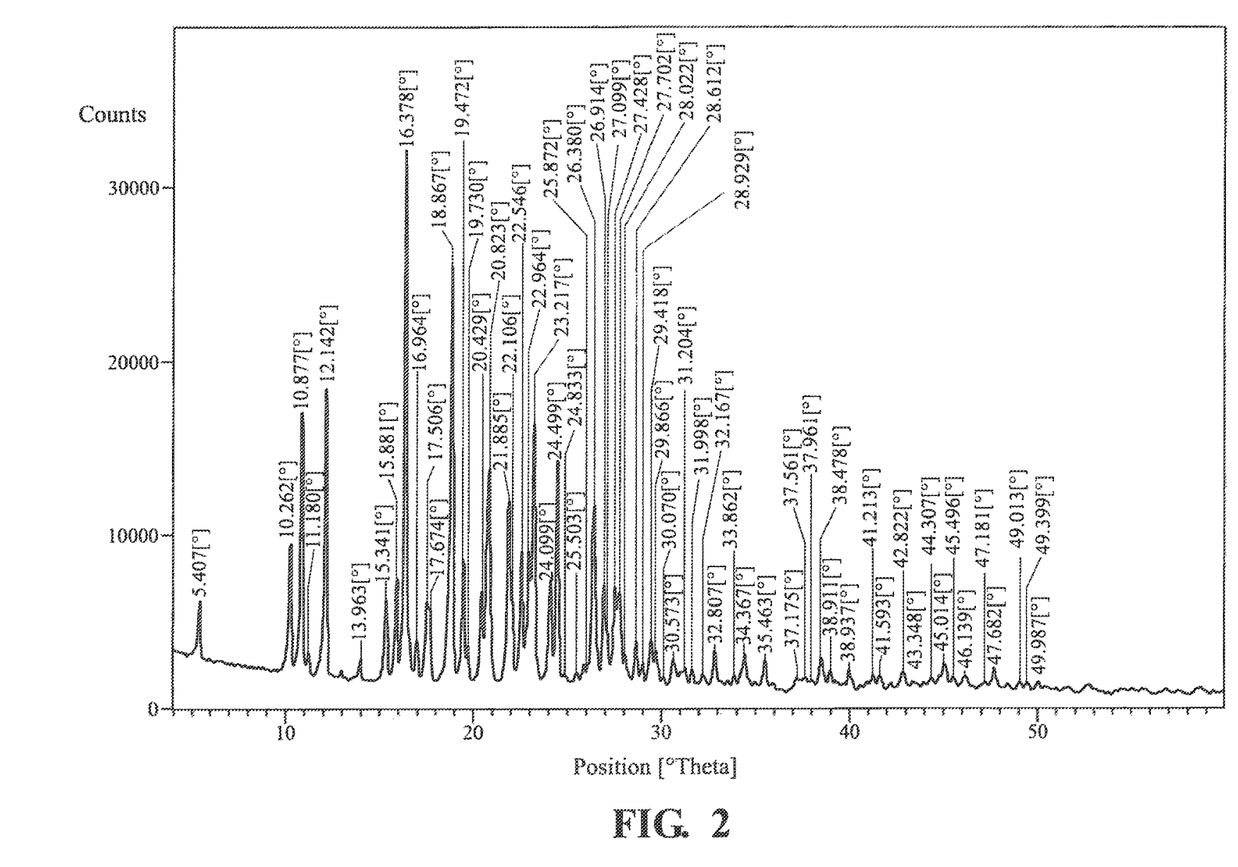
FIG. 2 is a X-ray powder diffractogram of an embodiment of crystalline modification I of mefenpyr-diethyl.

More particularly, the crystalline modification I of mefenpyr-diethyl of an embodiment of the invention is characterized by an X-ray powder diffractogram having at least three of the reflexes indicated above, in any combination. This means that the crystalline modification I of an embodiment of mefenpyr-diethyl can contain three or more of the reflexes indicated above in any combination of reflexes. For example, the crystalline modification I of an embodiment of mefenpyr-diethyl can contain at least reflexes (1), (2), and (3), or at least reflexes (2), (3), and (4), or reflexes (1), (3), and (4), or any other combination of at least three reflexes. Preferably, the crystalline modification I is one having at least four of the aforementioned reflexes, more preferably at least five, six, or seven, or eight of said reflexes, again in any combination. An X-ray powder diffractogram of the crystalline modification I of mefenpyr-diethyl is shown in FIG. 2, which will be described in detail hereinafter.

Further to X-ray diffraction analysis, the crystalline modification I of mefenpyr-diethyl according to an embodiment may be characterized by Infrared (IR) spectroscopy. The IR spectrum of the crystalline modification I is showed in FIG. 1 with characteristic bands at one or more of 3086.56, 2983.56, 2903.31, 1731.44 and 1719.50 cm$^{-1}$.

All IR spectra were obtained using the following acquisition parameters:

| | |
|---|---|
| FT-IR spectrometer | Bruker Tensor37 |
| Diamond ATR unit | from Specac |
| Wavelength range | 550-4000 cm$^{-1}$ |
| Resolution | 4 cm$^{-1}$ |
| Number of scans | 16 |

Figure 3:
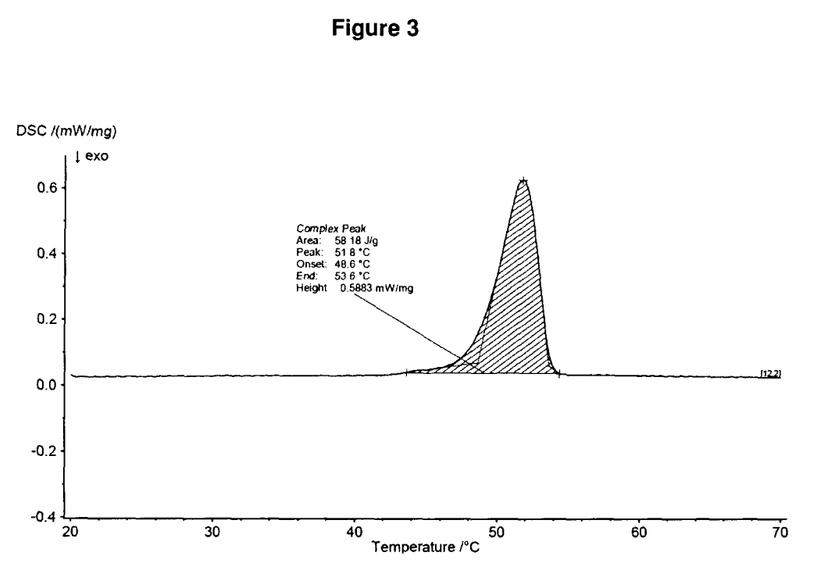
FIG. 3 is a Differential Scanning Calorimetry (DSC) scan spectrum of an embodiment of crystalline modification I of mefenpyr-diethyl.

The crystalline modification I of mefenpyr-diethyl according to an embodiment of the invention may be further characterized by differential scanning calorimetry (DSC). The DSC spectrum of the crystalline modification I of mefenpyr-diethyl exhibits an endothermic melting peak with onset at 48.6° C. and peak maximum at about 51.8° C. as shown in FIG. 3. As used herein, the terms "about 51.8° C." means a range of 50° C. to 54° C.

Methods for preparing amorphous mefenpyr-diethyl are known in the art. Amorphous mefenpyr-diethyl is manufactured and available on a commercial scale. A particularly suitable method for preparing amorphous mefenpyr-diethyl is described in U.S. Pat. No. 5,703,008, which is incorporated herein by reference for all purposes.

According to an embodiment of the invention, the crystalline modification I of mefenpyr-diethyl can be obtained by the processes below:

Mefenpyr-diethyl in amorphous state is dissolved and then crystallized from solvents.

In one aspect, the present invention provides a process for preparing a crystalline modification I of mefenpyr-diethyl comprising steps of:

i) preparing a solution of an amorphous mefenpyr-diethyl in a solvent;

ii) effecting crystallization of mefenpyr-diethyl from the solution to obtain a precipitate; and iii) isolating the precipitated crystalline modification I.

Suitable solvents for mefenpyr-diethyl crystalline modification I include acetonitrile, halogenated hydrocarbons (for example, chlorobenzene, bromobenzene, dichlorobenzene, chlorotoluene and trichlorobenzene), ethers (for example, ethyl propyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, methyl tert-butyl ether, tetrahydrofuran, methyltetrahydrofuran, dioxane, dichlorodiethyl ether, methyl-tetrahydrofuran, polyethers of ethylene oxide and/or propylene oxide), nitrated hydrocarbons (for example, nitromethane, nitroethane, nitropropane, nitrobenzene, chloronitrobenzene and o-nitrotoluene), aliphatic, cycloaliphatic or aromatic hydrocarbons (for example, pentane, n-hexane, n-heptane, n-octane, nonane), cymene, petroleum fractions having a boiling range of from 70° C. to 190° C., cyclohexane, methylcyclohexane, petroleum ether, ligroin, octane, benzene, toluene and xylene), esters (for example, malonates, acetic acid n-butyl ester (n-butyl acetate), methyl acetate, ethyl acetate, isobutyl acetate, dimethyl carbonate, diethyl carbonate, dibutyl carbonate and ethylene carbonate), and aliphatic alcohols (for example, methanol, ethanol, n-propanol, isopropanol, n-butanol and tert-amyl alcohol), and mixtures of these.

Preferred solvents include acetonitrile, ethers, aromatic hydrocarbons (such as benzene, toluene, xylene, chlorobenzene), esters and aliphatic alcohols and mixtures thereof. Particularly preferred solvents or solvent mixtures include diethyl ether, acetonitrile, toluene, methyl-tetrahydrofuran, diethyl carbonate, chlorobenzene, n-butyl acetate, isobutyl acetate, n-butanol, ethanol, ethyl malonate, methyl t-butyl ether, and their mixtures.

In a particular embodiment of the invention, it is preferred that the solvent is diethyl ether, acetonitrile, or mixture thereof.

Hence, according to a preferred embodiment in step (i), amorphous mefenpyr-diethyl is dissolved in a solvent comprising diethyl ether, or acetonitrile, or a mixture thereof.

In step (ii), mefenpyr-diethyl is crystallized from the solution. Techniques for effecting crystallization of mefenpyr-diethyl from the solution are known to those skilled in the art. For example, in an embodiment where the solution in step (i) is formed at elevated temperatures, crystallization may be effected by cooling the solution to room or ambient temperature, or to a temperature of around 0° C. to 20° C. In one preferred embodiment, crystallization is effected by concentrating the solution formed in step (i) of the process by removal of solvent.

Alternatively, or in addition thereto, seed crystals, in particular seed crystals of the aforementioned crystalline modification I of mefenpyr-diethyl, may be added to the solution formed in step (i), to facilitate and/or enhance crystallization.

The seed crystal amount added to the concentrated solution is typically in the range of 0.001 to 10% by weight, preferably 0.001 to 2.5% by weight, often 0.005 to 0.5% by weight based on the weight of mefenpyr-diethyl used for the preparation of concentrated solution in step (i). Preferably, the seed crystals are added to the concentrated solution at the temperature below the boiling point of the corresponding solvent or the solvent mixture.

It is preferred that the precipitate of mefenpyr-diethyl recovered during the crystallization stage is washed with a solvent for one or more times. Preferably, the solvent employed in the washing stage consists of one or more components of the solvent employed for forming the solution in step (i), as described hereinbefore. Diethyl ether and acetonitrile, and mixtures thereof are particularly suitable solvents for washing the recovered precipitate of mefenpyr-diethyl. The washing is usually carried out using the corresponding solvent or solvent mixture between room temperature and 0° C., depending on the solubility of the crystal, in order to minimize or avoid the loss of crystalline material in the corresponding washing solvent as much as possible.

The invention, in an embodiment, also relates to a composition comprising the crystalline modification I of mefenpyr-diethyl and sulfonylurea herbicides. The weight ratio of the mefenpyr-diethyl to sulfonylurea herbicides varies within wide limits and is preferably in a range of about 1:10 to about 10:1, in particular in a range of about 1:10 to about 5:1.

The amount of sulfonylurea herbicides in the formulation can be less than about 70% by weight of the formulation, preferably less than about 50% by weight of the formulation, particularly preferably about 25% by weight of the formulation.

The use of amorphous mefenpyr-diethyl as a safener for sulfonylurea herbicides is known in the art and is used on a commercial scale. The crystalline modification I of mefenpyr-diethyl is also active in reducing the phototoxicity of sulfonylurea herbicides when controlling weeds. Techniques of formulating and applying amorphous mefenpyr-diethyl and sulfonylurea herbicides are known in the art. Mefenpyr-diethyl in the crystalline modification I of the present invention may be formulated and applied in an analogous manner with sulfonylurea herbicides.

Accordingly, in a further aspect, the invention provides a herbicidal composition comprising mefenpyr-diethyl in the crystalline modification I, as defined hereinbefore, with sulfonylurea herbicides.

Accordingly, an embodiment of the invention furthermore provides processes for preparing compositions for controlling weeds using the crystalline modification I of mefenpyr-diethyl together with sulfonylurea herbicides.

The crystalline modification I of mefenpyr-diethyl together with sulfonylurea herbicides can be incorporated in a known manner to the customary formulations, such as suspension concentrates (SC), oil-based suspension concentrates (OD), water-soluble granules (SG), dispersible concentrates (DC), emulsifiable concentrates (EC), emulsion seed dressings, suspension seed dressings, granules (GR), microgranules (MG), suspoemulsions (SE) and water-dispersible granules (WG) using suitable herbicidally acceptable auxiliaries, carriers and solvents.

These formulations are prepared by mixing the crystalline modification I of mefenpyr-diethyl and sulfonylurea herbicides in amounts of each analogous to those used for amorphous mefenpyr-diethyl with customary additives, for example, liquid diluents, solid diluents, wetting agents, dispersants, thickening agent, antifoaming agents and other formulation ingredients.

Sulfonylurea herbicides suitable for safening by the crystalline modification I of mefenpyr-diethyl include, but are not limited to, amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl-sodium, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron and salts thereof, and mixtures thereof.

The following sulfonylureas are preferred for safening by the crystalline modification I of mefenpyr-diethyl in accordance with an embodiment of the invention: iodosulfuron-methyl-sodium, mesosulfuron-methyl, bensulfuron-methyl, flupyrsulfuron-methyl, metsulfuron-methyl, nicosulfuron, rimsulfuron, sulfometuron-methyl, thifensulfuron-methyl, tribenuron-methyl, halosulfuron-methyl and salts thereof, and mixtures thereof.

Liquid diluents include, but are not limited to, water, N,N-dimethylamide, dimethyl sulfoxide, N-alkylpyrrolidone, ethylene glycol, polypropylene glycol, propylene carbonate, dibasic esters, paraffines, alkylbenzenes, alkyl naphthalenes, glycerine, triacetin, oils of olive, castor, linseed, sesame, corn, peanut, cotton-seed, soybean, rape-seed and coconut, ketones such as cyclohexanone, 2-heptanone, isophorone and 4-hydroxy-4-methyl-2-pentanone, acetates such as hexyl acetate, heptyl acetate and octyl acetate, and alcohols such methanol, cyclohexanol, decanol, benzyl and tetrahydrofurfuryl alcohol, and mixtures of these.

Solid diluents can be water-soluble or water-insoluble. Water-soluble solid diluents include, but are not limited to, salts such as alkali metal phosphates (e.g., sodium dihydrogen phosphate), alkaline earth phosphates, sulfates of sodium, potassium, magnesium and zinc, sodium and potassium chloride, sodium acetate, sodium carbonate and sodium benzoate, and sugars and sugar derivatives such as sorbitol, lactose, sucrose and mannitol, and mixtures thereof. Examples of water-insoluble solid diluents include, but are not limited to clays, synthetic and diatomaceous silicas, calcium and magnesium silicates, titanium dioxide, aluminum, calcium and zinc oxide, and mixtures of these.

Wetting agents include, but are not limited to, alkyl sulfosuccinates, laureates, alkyl sulfates, phosphate esters, acetylenic diols, ethoxyfluornated alcohols, ethoxylated silicones, alkyl phenol ethyoxylates, benzene sulfonates, alkyl-substituted benzene sulfonates, alkyl a-olefin sulfonates, naphthalene sulfonates, alkyl-substituted napthalene sulfonates, condensates of naphthalene sulfonates and alkyl-substituted naphthalene sulfonates with formaldehyde, and alcohol ethoxylates, and mixtures of these. Alkyl naphthalene sulphonates, sodium salts are particularly useful for the composition of the invention Dispersants include, but are not limited to, sodium, calcium and ammonium salts of ligninsulfonates (optionally polyethoxylated); sodium and ammonium salts of maleic anhydride copolymers; sodium salts of condensed phenolsulfonic acid; and naphthalene sulfonate-formaldehyde condensates, and mixtures of these. Ligninsulfonates such as sodium ligninsulfonates are particularly useful for the composition of the invention. Naphthalene sulfonate-formaldehyde condensates, such as naphthalenesulfonic acid, polymers with formaldehyde, and sodium salts are particularly useful for the composition of an embodiment of the invention Thickening agents include, but are not limited to, guar gum, pectin, casein, carrageenan, xanthan gum, alginates, methylcellulose, hydroxyethylcellulose, hydroxypropylcellulose, and carboxymethylcellulose, and mixtures of these. Synthetic thickening agents include derivatives of the former categories, and also polyvinyl alcohols, polyacrylamides, polyvinylpyrrolidones, various polyethers, their copolymers as well as polyacrylic acids and their salts, and mixtures of these. Alkylpolyvinylpyrrolidones are particularly useful for the composition of the present invention Other formulation ingredients can also be used in the present invention such as dyes, drying agents, and the like. These ingredients are known to one skilled in the art.

The crystalline modification I of mefenpyr-diethyl according to an embodiment of the invention can be present in formulations and in its use forms, prepared from these formulations, and as a safener to reduce the phototoxicity of sulfonylurea herbicides.

All plants, plant parts, and surroundings thereof can be treated with the crystalline modification I of mefenpyr-diethyl in accordance with an embodiment of the invention. In the present context, plants are to be understood as meaning all plants and plant populations such as desired and undesired wild plants or crop plants (including naturally occurring crop plants). Crop plants can be plants which can be obtained by conventional breeding and optimization methods, by biotechnological and genetic engineering methods, or by combinations of these methods, including the transgenic plants and the plant cultivars which can or cannot be protected by plant breeders' rights. Plant parts are to be understood as meaning all parts and organs of plants above and below the ground, such as shoots, leaves, needles, stalks, stems, flowers, fruit bodies, fruits, seeds, roots, tubers and rhizomes. Harvested materials, and vegetative and generative propagation materials, for example, cutting, tubers, meristem tissues, rhizomes, offsets, seeds, single and multiple plant cells and any other plant tissues, are also included.

As used herein, the term "about," when used in connection with a numerical amount or range, means somewhat more or somewhat less than the stated numerical amount or range, to a deviation of ±10% of the stated numerical amount or endpoint of the range.

"Surrounding," as used herein, refers to the place on which the plants are growing, the place on which the plant propagation materials of the plants are sown or the place on which the plant propagation materials of the plants will be sown, or the environment near the plants.

The term "herbicidally effective amount" as used herein, refers to the quantity of such a compound or combination of such compounds that is capable of producing a controlling effect on the growth of plants. The controlling effects include all deviation from the natural development of the target plants, for example killing, retardation of one or more aspects of the development and growth of the plant, leaf burn, albinism, dwarfing and the like.

Treatment of the plants and plant parts with the compositions or formulations of the inventions according to the invention is carried out directly or by allowing the compositions or formulations to act on their surroundings, habitat or storage space by the customary treatment methods. Examples of these customary treatment methods include dipping, spraying, vaporizing, fogging, broadcasting, painting on in the case of propagation material, and applying one or more coats particularly in the case of seed.

All percentages are given in weight % unless otherwise indicated.

Embodiments of the invention will now be described by way of the following examples which are provided for illustrative purposes only, and not intended to limit the scope of the disclosure or of the appended claims.

EXAMPLES

Example 1: Preparation of Amorphous Mefenpyr-Diethyl in Accordance with the Disclosure of U.S. Pat. No. 5,703,008 (Example 3 with Modification)

22.8 g of ethyl methylacrylate and 14.8 g of ethyl-2-chloro-(2,4-dichlorophenylhydrazono)carboxylate were heated to 50° C.-60° C. 7.6 g of triethylamine were added dropwise to this mixture in the course of half an hour. Stirring was continued for 2 hours at 70° C., the mixture was allowed to cool, and the precipitate was filtered off with suction, and the filtrate was carefully concentrated under reduced pressure. 18.1 g of product was obtained.

Scheme 1. Synthesis of mefenpyr-diethyl

Figure 4:
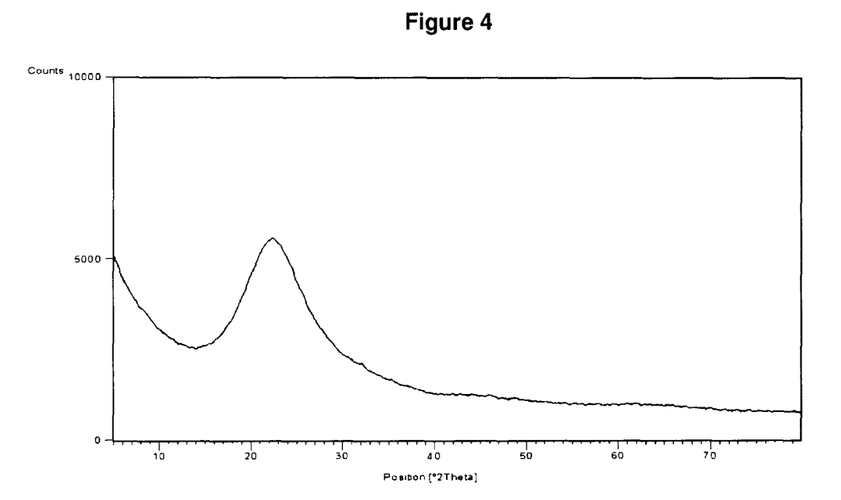
FIG. 4 is a X-ray diffractogram powder of amorphous mefenpyr-diethyl.

As shown in FIG. 4, the X-ray powder diffraction pattern of the resulting mefenpyr-diethyl product has no significant signals, which indicates the mefenpyr-diethyl product prepared in accordance with the disclosure of U.S. Pat. No. 5,703,008 is amorphous.

Example 2: Preparation of the Crystalline Modification I of Mefenpyr-Diethyl Crystallization from Diethyl Ether 10 ml diethyl ether was charged into the reactor to dissolve crude, amorphous mefenpyr-diethyl prepared in Example 1 under stirring. This process lasted for 2 hours under room temperature, and white solid precipitate appeared. The mixture was then cooled down to 0° C.-5° C. and maintained at this temperature for 1 hour to allow complete crystallization. After that, the mixture was centrifuged. The filter cake was washed with diethyl ether. The resulting solid was dried under high vacuum to give crystals of pure mefenpyr-diethyl technical (Purity: 98%).

The crystals were characterized as being of the crystalline modification I of mefenpyr-diethyl using IR spectrometry, X-ray powder diffraction and DSC respectively.

Figure 1:
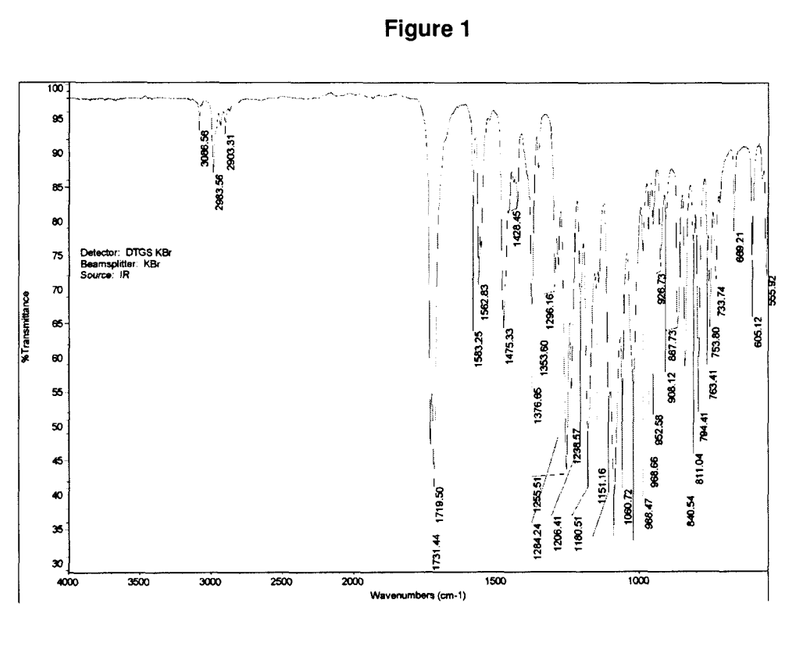
FIG. 1 is an infrared (IR) spectrum of an embodiment of crystalline modification I of mefenpyr-diethyl.

The IR spectrum of the crystalline modification I of mefenpyr-diethyl is set out in FIG. 1. The IR spectrum exhibits characteristic peaks at 3086.56, 2983.56, 2903.31, 1731.44 and 1719.50 $cm^{-1}$.

The melting point of the product was measured by DSC and exhibits a an endothermic melting peak with onset at 48.6° C. and peak maximum at about 51.8° C. as shown in FIG. 3.

The crystalline modification I of mefenpyr-diethyl has the X-ray powder diffractogram shown in FIG. 2 with the reflexes listed in Table 1 below. The X-ray powder diffractogram were taken using a diffractometer in reflection geometry in the range from 3°-60° with increments of 0.03° using Cu-Kα radiation at 25° C.

TABLE 1

Crystalline modification I

| 2 θ (°) | d (Å) |
|---|---|
| 7.76 ± 0.2 | 11.39 ± 0.05 |
| 10.76 ± 0.2 | 8.22 ± 0.05 |
| 14.00 ± 0.2 | 6.33 ± 0.05 |
| 14.85 ± 0.2 | 5.97 ± 0.05 |
| 16.67 ± 0.2 | 5.32 ± 0.05 |
| 19.49 ± 0.2 | 4.55 ± 0.05 |
| 23.10 ± 0.2 | 3.85 ± 0.05 |
| 23.75 ± 0.2 | 3.75 ± 0.05 |
| 24.48 ± 0.2 | 3.64 ± 0.05 |
| 26.02 ± 0.2 | 3.43 ± 0.05 |
| 26.27 ± 0.2 | 3.39 ± 0.05 |
| 28.49 ± 0.2 | 3.13 ± 0.05 |

Example 3: Preparation of the Crystalline Modification I of Mefenpyr-Diethyl

Crystallization from Acetonitrile 10 ml acetonitrile was charged into the reactor to dissolve crude, amorphous mefenpyr-diethyl prepared in Example 1 under stirring. This process lasted for 2 hours under room temperature, and white solid precipitate appeared. The mixture was then cooled down to 0° C.-5° C. and maintained at this temperature for 1 hour to allow complete crystallization. After that, the mixture was centrifuged. The filter cake was washed with some acetonitrile. The resulting solid was dried under high vacuum to give crystals of pure mefenpyr-diethyl technical (Purity: 98%).

The crystals were characterized as being the crystalline modification I of mefenpyr-diethyl using IR spectrometry, X-ray powder diffraction and DSC as described in Example 2.

Example 4: Preparation of Oil Based Suspension Concentrate (OD) Formulation

All the components listed in Table 2 below were mixed uniformly and ground with a Dyno-Mill (manufactured by Willy A. Bachofen AG) to obtain an oil based suspension concentrate.

TABLE 2

| Ingredients | Weights % | | Function |
|---|---|---|---|
| Mefenpyr-diethyl, crystalline modification I, 98% (prepared in Example 2) | 10.20 | 0.00 | Safener |
| Amorphous mefenpyr-diethyl (prepared in Example 1) | 0.00 | 10.20 | Safener |
| Iodosulfuron-methyl-sodium, 98% | 40.80 | 40.80 | Active compound |
| Modified polyether-polysiloxane | 0.5 | 0.5 | Antifoaming agent |
| Ethoxylated castor oil | 15 | 15 | Emulsifier |
| Sodium alkylnaphthalenesulfonate, formaldehyde condensateSodium | 5 | 5 | Dispersing agent |
| Silica | 2 | 2 | Thickening agent |
| Corn oil | Balance to 100% | Balance to 100% | Carrier |

Example 5: Preparation of Soluble Granules (SG)

All the components listed in Table 3 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 3

| Ingredients | Weights % | | Function |
|---|---|---|---|
| Mefenpyr-diethyl, crystalline modification I, 98% (prepared in Example 2) | 7.14 | 0.00 | Safener |
| Amorphous mefenpyr-diethyl (prepared in Example 1) | 0.00 | 7.14 | Safener |
| Mesosulfuron-methyl, 98% | 25.51 | 25.51 | Active compound |
| Lignosulfonic acid, sodium salt, (REAX ® 88B) | 15.00 | 15.00 | Antifoaming agent |
| Sodium lauryl sulfate | 0.5 | 0.5 | Wetting agent |
| Sodium hydrogen carbonate | 2.00 | 2.00 | Filler |
| Potassium sulfate | Balance to 100% | Balance to 100% | carrier |

Example 6: Preparation of Water Dispersible Granules (WG)

All the components listed in Table 4 below were mixed, blended and milled in a high-speed rotary mill. Sufficient water was added to obtain an extrudable paste. The paste was extruded through a die or screen to form an extrudate. The wet extrudate was dried at 70° C. in a vacuum oven and then sifted through 0.71 mm-2 mm screens to obtain the product granules.

TABLE 4

| Ingredients | Weights % | | Function |
|---|---|---|---|
| Mefenpyr-diethyl, crystalline modification I, 98% (prepared in Example 2) | 7.14 | 0.00 | Safener |
| Amorphous mefenpyr-diethyl (prepared in Example 1) | 0.00 | 7.14 | Safener |
| Iodosulfuron-methyl-sodium, 98% | 25.51 | 25.51 | Active compound |
| Alkyl naphthalene sulphonate, sodium salt (Akzo Nobel) | 2 | 2 | Wetting agent |
| Lignosulfonic acid, sodium salt, REAX ® 88B) | 15 | 15 | Dispersing agent |
| Naphthalenesulfonic acid, polymer with formaldehyde, sodium salt (TAMOL ® NN8906) | 6 | 6 | Dispersing agent |
| Non-ionic aqueous emulsion of Polydimethylsiloxanes | 1 | 1 | Antifoaming agent |
| Mannitol | Balance to 100% | Balance to 100% | Carrier |

Example 7: Stability Test

The stability of the mefenpyr-diethyl in these compositions was determined by aging samples in heated ovens having the same atmosphere therein, and then comparing the mefenpyr-diethyl content before and after aging to determine relative percentage of hydrolysis (RPH). RPH was calculated by the following equation:

$$RPH = \frac{\text{(The final weight \% of mefenpyr-diethyl} - \text{The initial weight \% of mefenpyr-diethyl)}}{\text{The initial weight \% of mefenpyr-diethyl}} \times 100\%$$

Mefenpyr-diethyl content was determined by assaying the compositions with high-pressure liquid chromatography (HPLC) using reverse phase columns and eluants.

Samples prepared in Examples 4, 5 and 6 were stored at 54° C. for 1 week. The procedures are followed according to CIPAC MT 46.3. The concentration of mefenpyr-diethyl was measured at the end of each storage time by HPLC. The results are listed in Table 5.

TABLE 5

| Sample | Compound | Weight (%) of mefenpyr-diethyl | RPH % |
|---|---|---|---|
| Example 4 | Mefenpyr-diethyl, crystalline modification I | 10 | 0 |
|  | Amorphous mefenpyr-diethyl | 10 | 50 |
| Example 5 | Mefenpyr-diethyl, crystalline modification I | 7 | 0 |
|  | Amorphous mefenpyr-diethyl | 7 | 40 |
| Example 6 | Mefenpyr-diethyl, crystalline modification I | 7 | 0 |
|  | Amorphous mefenpyr-diethyl | 7 | 45 |

The invention claimed is:

1. A crystalline modification I of mefenpyr-diethyl, exhibiting each of the following reflexes in an X-ray powder diffractogram recorded using Cu-Kα radiation at 25° C.:

$2\theta=7.76\pm0.2$ (1)

$2\theta=10.76\pm0.2$ (2)

$2\theta=14.00\pm0.2$ (3)

$2\theta=14.85\pm0.2$ (4)

$2\theta=16.67\pm0.2$ (5)

$2\theta=19.49\pm0.2$ (6)

$2\theta=23.10\pm0.2$ (7)

$2\theta=23.75\pm0.2$ (8)

$2\theta=24.48\pm0.2$ (9)

$2\theta=26.02\pm0.2$ (10)

$2\theta=26.27\pm0.2$ (11)

$2\theta=28.49\pm0.2$ (12).

2. The crystalline modification I of mefenpyr-diethyl according to claim 1, exhibiting IR spectrum with one or more of the characteristic bands at 3086.56, 2983.56, 2903.31, 1731.44 and 1719.50 cm$^{-1}$.

3. The crystalline modification I of mefenpyr-diethyl according to claim 1, exhibiting a Differential Scanning calorimeter (DSC) thermogram exhibits an endothermic melting peak with onset at 48.6° C. and peak maximum at about 50° C. to 54° C.

4. A process for the preparation of a crystalline modification I of mefenpyr-diethyl according to claim 1, comprising:
   i) preparing a solution of an amorphous mefenpyr-diethyl in a solvent, wherein the solvent comprises diethyl ether, acetonitrile, or a combination thereof;
   ii) effecting crystallization of mefenpyr-diethyl from the solution to obtain a solid precipitate; and
   iii) isolating the precipitated crystalline modification I.

5. A composition comprising a safening amount of the crystalline modification I of mefenpyr-diethyl according to claim 1, a herbicidally effective amount of at least one sulfonylurea herbicide, and an effective amount of at least one auxiliary.

6. The composition in claim 5, wherein the composition is formulated as a suspension concentrate (SC), an oil-based suspension concentrate (OD), a water-soluble granule (SG), a dispersible concentrate (DC), an emulsifiable concentrate (EC), an emulsion seed dressing, a suspension seed dressing, a granule (GR), a microgranule (MG), a suspoemulsion (SE) or a water-dispersible granule (WG).

7. The composition according to claim 6, wherein the composition is formulated as an oil-based suspension concentrate (OD).

8. The composition according to claim 6, wherein the composition is formulated as a water-soluble granule (SG).

9. The composition according to claim 6, in the form of a water-dispersible granule (WG).

10. The composition according to claim 5, wherein the auxiliary is selected from the group consisting of one or more of a solvent, a diluent, a wetting agent, a dispersant, an antifoaming agent and a thickening agent.

11. The composition according to claim 5, where the weight ratio of the mefenpyr-diethyl to sulfonylurea herbicides is in a range of about 1:10 to about 10:1.

12. The composition according to claim 5, where the weight ratio of the mefenpyr-diethyl to sulfonylurea herbicides is in a range of about 1:10 to about 5:1.

13. A method of controlling undesirable plant growth, comprising applying to the plant an effective amount of a composition according to claim 5.

14. The composition according to claim 5, wherein the sulfonylurea herbicide includes one or more selected from the group consisting of amidosulfuron, azimsulfuron, bensulfuron-methyl, chlorimuron-ethyl, chlorsulfuron, cinosulfuron, cyclosulfamuron, ethametsulfuron-methyl, ethoxysulfuron, flupyrsulfuron-methyl, flazasulfuron, foramsulfuron, halosulfuron-methyl, imazosulfuron, iodosulfuron-methyl-sodium, mesosulfuron-methyl, metsulfuron-methyl, nicosulfuron, oxasulfuron, primisulfuron-methyl, prosulfuron, pyrazosulfuron-ethyl, rimsulfuron, sulfometuron-methyl, sulfosulfuron, thifensulfuron-methyl, triasulfuron, tribenuron-methyl, trifloxysulfuron, triflusulfuron-methyl, tritosulfuron and salts thereof, and mixtures thereof.

15. The composition according to claim 14, wherein the sulfonylurea herbicide includes one or more selected from the group consisting of iodosulfuron-methyl-sodium, mesosulfuron-methyl, bensulfuron-methyl, flupyrsulfuron-methyl, metsulfuron-methyl, nicosulfuron, rimsulfuron, sulfometuron-methyl, thifensulfuron-methyl, tribenuron-methyl, halosulfuron-methyl and salts thereof, and mixtures thereof.

* * * * *